(12) United States Patent
Peña Cabrera et al.

(10) Patent No.: US 8,710,220 B2
(45) Date of Patent: Apr. 29, 2014

(54) SYNTHESIS OF 8-AMINO BORON DIPYRROMETHENES HAVING BLUE FLUORESCENCE

(75) Inventors: Eduardo Peña Cabrera, Guanajuato (MX); César Fernando Azael, Guanajuato (MX); Juan Orlando Flores, Guanajuato (MX)

(73) Assignee: Universidad de Guanajuato, Guanajuato (MX)

( * ) Notice: Subject to any disclaimer, the term of this patent is extended or adjusted under 35 U.S.C. 154(b) by 0 days.

(21) Appl. No.: 13/512,734

(22) PCT Filed: Dec. 10, 2010

(86) PCT No.: PCT/MX2010/000151
§ 371 (c)(1),
(2), (4) Date: May 30, 2012

(87) PCT Pub. No.: WO2011/071360
PCT Pub. Date: Jun. 16, 2011

(65) Prior Publication Data
US 2012/0253050 A1    Oct. 4, 2012

(30) Foreign Application Priority Data
Dec. 10, 2009   (MX) .................. MX/A/2009/013486

(51) Int. Cl.
*C07F 5/02*   (2006.01)

(52) U.S. Cl.
USPC ........................................................ 544/229

(58) Field of Classification Search
USPC ........................................................ 544/229
See application file for complete search history.

(56) References Cited

U.S. PATENT DOCUMENTS 3,857,793 A   12/1974  Pappalardo et al.
7,981,637 B2   7/2011  Miyawaki et al.

FOREIGN PATENT DOCUMENTS

WO   2005118606 A1   12/2005

OTHER PUBLICATIONS

Gomez-Duran, et al. Chem. Commun., 2010, 46, 5103-5105.*

(Continued)

*Primary Examiner* — Shawquia Young
(74) *Attorney, Agent, or Firm* — Panitch Schwarze Belisario & Nadel LLP

(57) ABSTRACT

A family of six 8-amino boron dipyrromethenes having Formulas 1, 2, 3, 4, 6, and 7 has been prepared. The presence of the amine group alters the emission properties of the boron dipyrromethene, such that these compounds are characterized by unexpected blue fluorescence, providing for potential use as lasers. The compound having formula 1 has very high quantum yield. The 8-amino boron dipyrromethenes are prepared in a straightforward, high yield synthesis by substituting an amine group for the thiomethyl group at the 8 position in 8-thiomethyl boron dipyrromethene. The compounds having Formulas 6 and 7 may be used to incorporate peptides and proteins, thus providing biomolecules marked with fluorescent fragments.

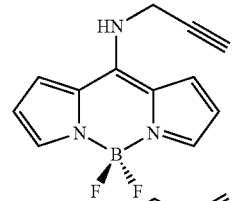

Formula 1

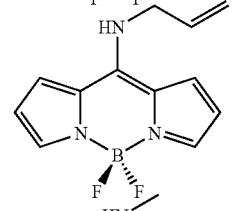

Formula 2

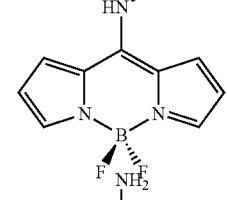

Formula 3

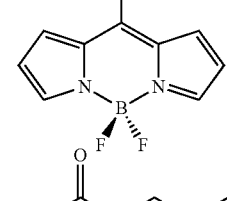

Formula 4

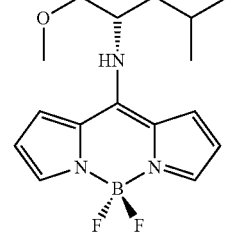

Formula 6

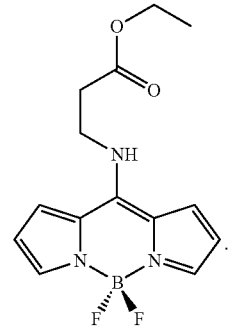

Formula 7

11 Claims, 2 Drawing Sheets

(56) References Cited

OTHER PUBLICATIONS

Sathyamoorthi et al, "Fluorescent Tricyclic Beta-Azavinamidine-BF2 Complexes", Heteroatom Chemistry, vol. 4, No. 6, pp. 603-608 (1993).

Ross et al, "Biimidazol-2-yl-BF2 Complexes", Heteroatom Chemistry, vol. 4, No. 6, pp. 609-612 (1993).

* cited by examiner

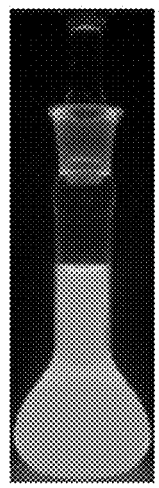 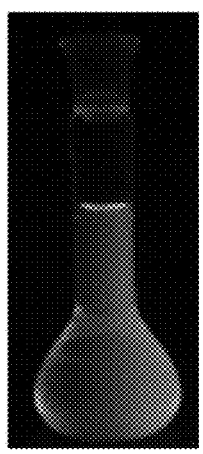 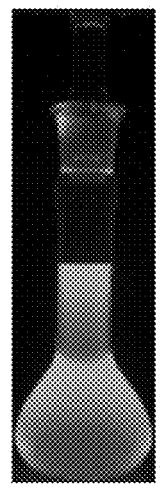 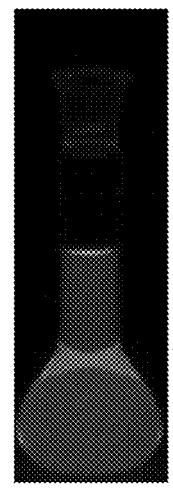
Figure 1     Figure 2     Figure 3     Figure 4
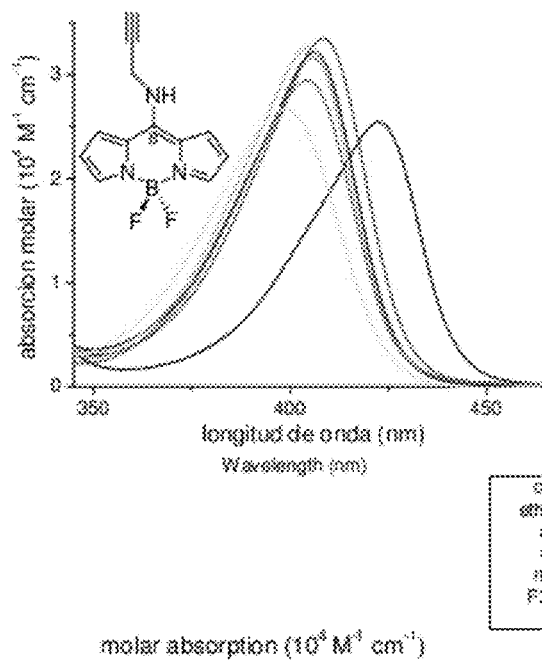 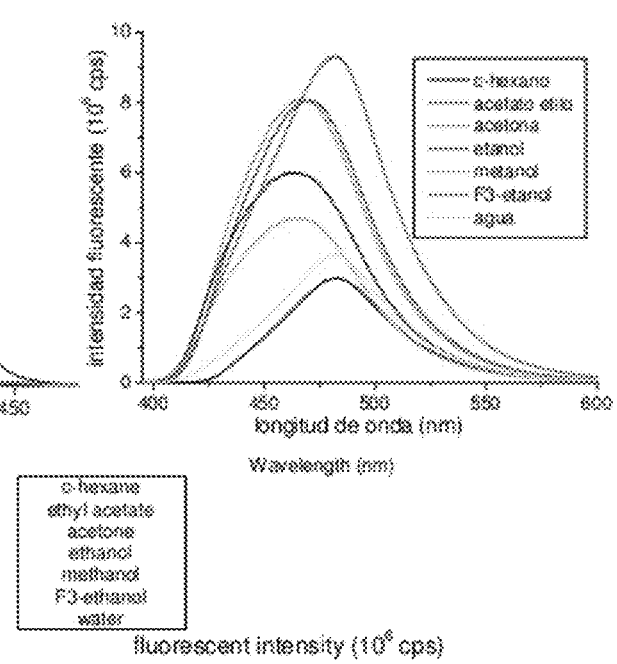
Figure 5

SYNTHESIS OF 8-AMINO BORON DIPYRROMETHENES HAVING BLUE FLUORESCENCE

CROSS-REFERENCE TO RELATED APPLICATIONS

This application is a Section 371 of International Application No. PCT/MX2010/000151, filed Dec. 10, 2010, which was published in the Spanish language on Jun. 16, 2011 under International Publication No. WO 2011/071360 A2, and the disclosure of which is incorporated herein by reference.

BACKGROUND OF THE INVENTION

Since their discovery in 1968, boron dipyrromethenes have been synthesized by complex methodologies which involve several steps, long reaction times, tedious purification, and tow yields, As time passed, techniques for obtaining these compounds were improved. While compounds exhibiting fluorescence in a large range of colors under UVC light (280 nm-200 nm) have been obtained, compounds exhibiting blue fluorescence and its nearby colors have not been reported. Ten years ago, Boyer and collaborators tried to synthesize blue boron dipyrromethenes (*Heteroat. Chem.* 4, 603 (1993) and *Heteroat. Chem* 4, 609 (1993)). In these experiments, the chromophore structure was drastically modified to decrease dislocation, yet Boyer still did not obtain highly fluorescent derivatives or compounds having high laser efficiencies.

There are no reports of boron dipyrromethenes with blue florescence. Other blue emitting compounds are known, which have similar applications to the compounds according to the invention. However, as reported in WO 2005/118606 of Konno et al., these compounds are more complex molecules with a larger number of atoms than the inventive compounds and require very complicated synthesis processes which require more hours of laboratory work and more complex molecules. Such compounds emit at 470 nm with a low quantum yield not higher than $\phi=0.8$ in tetrahydrofuran.

Miyawaki et al. (WO 2004/111236) reports proteins that fluoresce in the border area of the blue range (480 nm). However, this type of blue fluorescent protein is severely limited because its use is especially the biological area, is limited to certain mediums, and does not have a very high quantum yield ($\phi=0.68$).

Finally, there are known compounds that are patented for laser use (see U.S. Pat. No. 3,857,793 of Pappalardo et al.). For example, perylene, which emits at 410 nm in cyclohexane and has a quantum yield of $\phi=0.94$, is a 5 ring compound. P-terphenyl has an emission at 290 nm in cyclohexane and a 0.93 quantum yield. 9,10-diphenylanthracene is a compound with a high 1.0 quantum yield, but this compound fluoresces at 350 nm, an emission which does not correspond to blue. Accordingly, none of these compounds that are known for use in lasers emits within the blue fluorescent range.

BRIEF SUMMARY OF THE INVENTION

The invention is directed to the synthesis of 8-amino boron dipyrromethenes. These compounds have the special characteristic of fluorescing with blue color, especially propargyl-amino-boron-dipyrromethene (Formula 1), which fluoresces with the greatest intensity. This characteristic makes them unique in their kind, because there are no records of any boron dipyrromethene derivative compounds that fluoresce within the blue region of the electromagnetic radiation spectrum. The invention is specifically directed to six amino boron dipyrromethene compounds that fluoresce between 480 nm and 437 nm, including blue fluorescence (470 nm to 450 nm) and its near regions (10 nm above or below the blue region). One of these compounds, propargyl-amino-boron-dipyrromethenes (Formula 1) has the highest quantum yield. Further, the possibility of a greater number of substituted amines in the 8 position could create a wider range of blue emission.

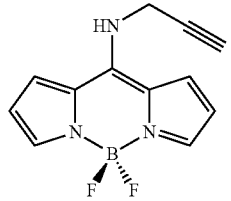

Formula 1

It has been found that an amino group directly attached to a chromophore creates new absorption and emission bands within the blue region of the visible spectrum, thus covering a spectral range unexplored to date with derivatives based on the boron dipyrromethene structure. The synthetic method according to the invention is very simple, with high chemical yields of around 90%, and produces compounds having high quantum yield (e.g., 0.94 for propargyl-amino-boron-dipyrromethenes (Formula 1)). A high chemical yield indicates that almost all the starting material has been converted into the desired product, whereas quantum yield is the ratio between emitted photons and absorbed photons.

Another advantage of these compounds is their structure, which is relatively simple. The compounds contain small end-functionalized groups, meaning that they do not have molecules with a large amount of atoms anchored to position 8, which results in ease of synthesis.

The invention claiming protection is a family of 8-amino boron dipyrromethenes, including 8-propargyl-amino-boron-dipyrromethene (Formula 1), 8-allyl-amino-boron-dipyrromethene (Formula 2), 8-methyl-amino-boron-dipyrromethene (Formula 3), 8-amino-boron-dipyrromethene (Formula 4), methyl ester of 8-L-leucine dipyrromethene (Formula 6), and ethylic ester from 8-β-alanine dipyrromethene (Formula 7), and their synthesis process, which is very general and simple.

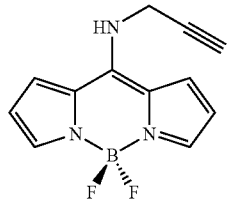

Formula 1

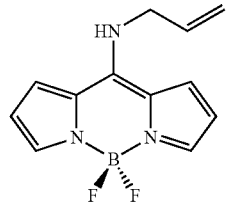

Formula 2

-continued

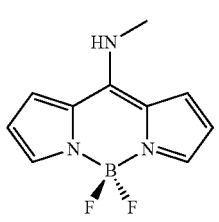
Formula 3

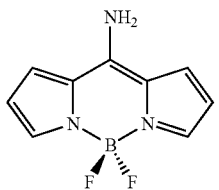
Formula 4

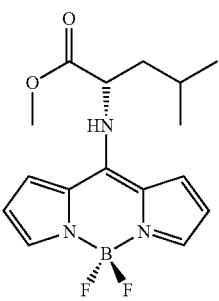
Formula 6

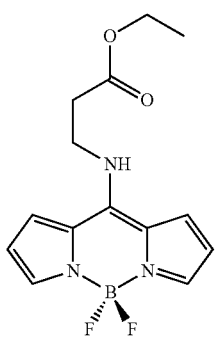
Formula 7

The invention is also directed to a method for replacing the thiomethyl group in 8-thiomethyl boron dipyrromethene starting material (Formula 5) with an amine or ammonium source. Due to the electronegativity of nitrogen and the free electron pair, these amine and ammonium sources are strong enough nucleophiles to displace the thiomethyl group without any assistance from a base. The thiomethyl displacement reaction proceeds via a carbon-carbon Liebskind-Srogl coupling. Utilization of a variety of amine and ammonium sources leads to a wide variety of compounds fluorescing in different areas of the electromagnetic spectrum regions.

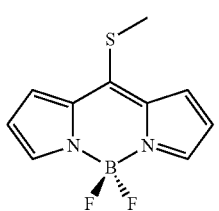
Formula 5

It is worth noting there are no general syntheses reported for obtaining 8-amino boron dipyrromethenes, let alone for compounds that fluoresce within the blue region of the electromagnetic spectrum. Using the method of the invention, a family of 8-amino boron dipyrromethenes which fluoresce in the blue region of the electromagnetic spectrum and have desirable laser properties may be synthesized in a short reaction time (from 50 to 120 minutes) and with chemical yields of 90 to 94%.

As already mentioned, the benefits of this invention for the synthesis of 8-amino boron dipyrromethenes are the reaction conditions needed to perform a simple nucleophilic substitution, which involves replacing a low nucleophile atom with one with higher nucleophilicity. Nucleophilicity refers to the capacity of an atom to donate electron pairs. In this case, the nitrogen in the amines has higher electronegativity and is more nucleophilic that the thiomethyl group because it has available electron pairs and, therefore, substitutes for the less electronegative sulfur which does not have any available electron pairs to generate greater nucleophile activity. The reaction is performed at a temperature of 25° C. (except for BDP amines) and does not require any external agent to act as a catalyst.

The reaction is typically performed using dichloromethane as a moist solvent. That is, the solvent is used without first performing any treatment for eliminating the small amount of water that may be present in the solvent. Typically, molecular sieves are used to eliminate water from solvents and the dried solvents are then kept under a nitrogen atmosphere. Besides using this moist solvent, it is common in reactions placing any group in position 8 to perform the reaction in an inert atmosphere, by placing the reaction vessel in a nitrogen atmosphere.

Another important advantage of the reaction according to the invention is its purification step, which is very simple. Purification is a process for obtaining a pure product without any impurities that can drag on the reaction, such as solvents or other by-products. For these compounds, the pure products are obtained through crystallization. Crystallization consists of immersing the product in the least amount of a solvent so that it dissolves completely, then adding another solvent that dissolves the impurities but not the product. A pure product is obtained without any by-product or traces of solvent. It is not necessary to perform a columned purification of the products of the invention because the reaction is clean with no by-products that are hard to remove other than the thiomethyl, which is easily eliminated because of its low boiling point.

Therefore, the novelty of this invention is the 8-amino boron dipyrromethene synthesis process. These compounds have unique blue fluorescence attributes never before recorded, and new absorption and emission characteristics not known in boron dipyrromethene derivatives. In particular, propargyl-amino-boron-dipyrromethene has characteristics that make it suitable for use in lasers.

The technique developed to displace the thiomethyl group is very efficient and simple. Currently, only a group of amino derivatives have been prepared, but these compounds are indicative of the potential to utilize alternative amine compounds with similar characteristics as the amine derivatives used. Thus, the variety of compounds that may be obtained from the synthesis of these compounds is augmented. The technique is very simple and shall help to increase this derivative family.

Our research group develops dyes with fluorescent properties in a great variety of colors. When preparing the amino boron dipyrromethenes, a photophysical study was performed on propargyl-amino-boron-dipyrromethene. Due to its high quantum yield of 0.94 and blue fluorescence, this compound has characteristics that make it suitable for use in a laser. In addition, the synthesis of the derivatives with amine esters (Formulas 6 and 7) provides for the design of biological applications, such as integration to proteins.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 1 depicts a flask containing 8-propargyl-amino-boron-dipyrromethene (Formula 1), having blue fluorescence with an emission at 469.3 nm and a quantum yield of 0.94;

FIG. 2 depicts a flask containing 8-allyl-amino-boron-dipyrromethene (Formula 2), having blue fluorescence with an emission at 456 nm;

FIG. 3 depicts a flask containing 8-methyl-amino-boron-dipyrromethene (Formula 3), having blue fluorescence at 440 nm;

FIG. 4 depicts a flask containing 8-amino boron dipyrromethene (Formula 4), having blue fluorescence at 437.5 with a quantum yield of 0.92;

FIG. 5 includes absorption and emission spectra for 8-propargyl-amino-boron-dipyrromethene in different solvents.

DETAILED DESCRIPTION OF THE INVENTION

Figure 6:
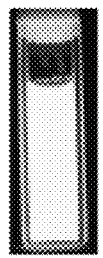
FIG. 6 depicts a cuvette containing starting material thiomethyl boron dipyrromethene showing its fluorescence.

The invention is directed to a family of six 8-amino boron dipyrromethenes having Formulas 1, 2, 3, 4, 6, and 7: propargyl-amino-boron-dipyrromethene (Formula 1), 8-allyl-amino-boron-dipyrromethene (Formula 2), 8-methyl-amino-boron-dipyrromethene (Formula 3); 8-amino-boron-dipyrromethene (Formula 4), methyl ester of 8-L-leucine dipyrromethene (Formula 6), and ethylic ester from 8-l3-alanine dipyrromethene (Formula 7).

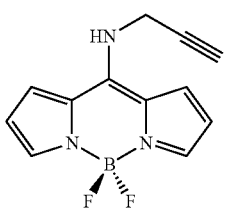

Formula 1

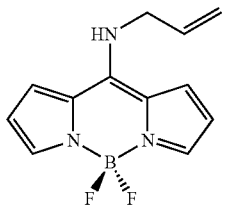

Formula 2

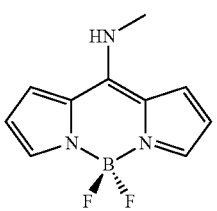

Formula 3

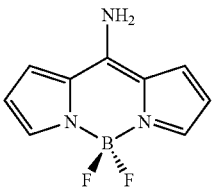

Formula 4

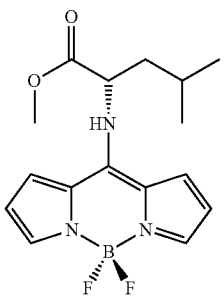

Formula 6

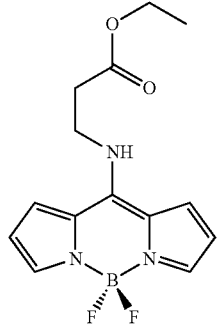

Formula 7

These compounds are prepared by substituting the thiomethyl group in thiomethyl boron dipyrromethene (Formula 5) with an amine or ammonium source.

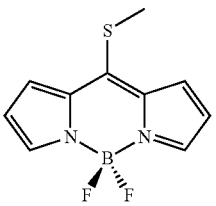

Formula 5

Four different amine or ammonium sources, propargylamine, allylamine, methylamine and ammonium acetate, were used to perform the substitution at position 8 of the thiomethyl boron dipyrromethene to create the corresponding amino boron dipyrromethenes 1, 2, 3, and 4.

This substitution is executed by combining one equivalent of thiomethyl boron dipyrromethene with 1.5 equivalents of the desired amine or ammonium source (for ammonium acetate two equivalents are required). The preferred solvent for the reactions is dichloromethane, except for the reaction with ammonium acetate, in which a 1:1 methanol:water solution is the preferred solvent.

The invention will now be described in conjunction with the following, non-limiting examples.

EXAMPLE 1

Synthesis of Propargyl-amino-boron-dipyrromethene (Formula 1)

Propargyl-amino-boron-dipyrromethene (Formula 1) was synthesized according to Reaction 1 as follows.

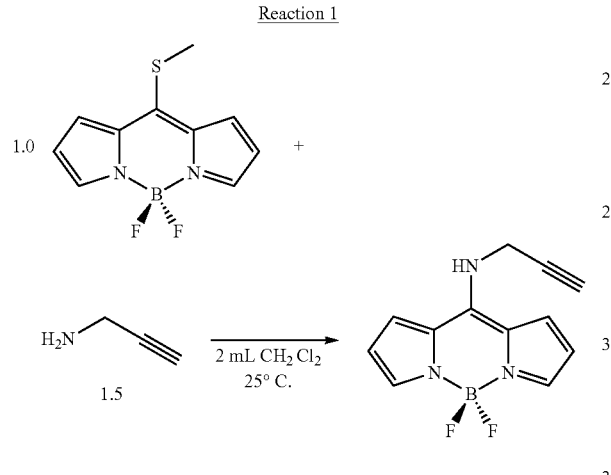

Reaction 1

1.0 equivalent (100 mg, 0.4201 mmol) of thiomethyl boron dipyrromethene was placed in a 50 mL flask and dissolved with 2 mL of dichloromethane. Subsequently, 1.5 equivalents of propargylamine (34.7 mg, 0.6302 mmol) were added. The reaction mixture was stirred using a magnetic stirrer over a hot plate stirrer at 25° C. The reaction was completed in 60 minutes with a 94% yield. It materialized as yellow crystals with yellow fluorescence. CCD (30% AcOEt/Hexanes) $R_f$=0.17 cm; UV-Vis: $\lambda_{abs}$=404.8 $\lambda_{flu}$=464 (methanol) p.d. 176.0-178.0° C.; IR (KBr, cm$^{-1}$): 633, 659, 732, 763, 1073, 1106, 1227, 1389, 1402, 1554, 1592, 3282, 3363, 3379. $^1$H NMR (200 MHz, CDCl$_3$) δ: 2.56(1H, m, J=2.6 Hz), 4.52 (2H, m, J=2.73Hz), 6.51 (2H, s), 6.70 (1H, s), 7.13 (2H, s), 7.67 (2H, s); $^{13}$C NMR (75.5 MHz, (CD$_3$)$_2$CO), δ: 36.8, 75.8, 78.0, 114.4, 115.7, 117.5, 122.9, 125.7, 126.2, 133.0, 136.3, 149.5.

The compound was analyzed in different solvents to determine its photophysical properties. The results are shown in Table 1. It can be seen that fluorescence varied from 463 nm to 481.5 nm, exhibiting the highest quantum yield in ethyl acetate with a 0.94 yield.

TABLE 1

Propargyl-amino-boron-dipyrromethene photophysics in several solvents

| Solvent | $\lambda_{abs}$ (nm) | $\epsilon_{max}$ (10$^4$M$^{-1}$cm$^{-1}$) | $\lambda_{flu}$ (nm) | $\Delta\nu_{St}$ (cm$^{-1}$) | φ | τ (ns) |
| --- | --- | --- | --- | --- | --- | --- |
| Water | 398.2 | 2.6 | 481.5 | 4345 | 0.32 | 2.00* |
| F$_3$-ethanol | 404.0 | 2.9 | 480.7 | 3950 | 0.88 | 6.34* |
| Methanol | 404.8 | 3.3 | 464.5 | 3175 | 0.52 | 3.22 |
| Ethanol | 406.4 | 3.2 | 463.0 | 3010 | 0.66 | 3.81 |

TABLE 1-continued

Propargyl-amino-boron-dipyrromethene photophysics in several solvents

| Solvent | $\lambda_{abs}$ (nm) | $\epsilon_{max}$ (10$^4$M$^{-1}$cm$^{-1}$) | $\lambda_{flu}$ (nm) | $\Delta\nu_{St}$ (cm$^{-1}$) | φ | τ (ns) |
| --- | --- | --- | --- | --- | --- | --- |
| Acetone | 406.0 | 3.1 | 466.5 | 3195 | 0.86 | 4.92 |
| Ethyl acetate | 408.4 | 3.3 | 469.3 | 3175 | 0.94 | 5.13 |
| c-hexane | 422.4 | 2.5 | 482.2 | 2935 | 0.93 | 5.34* |

EXAMPLE 2

Synthesis of 8-allyl-amino-boron-dipyrromethene (Formula 2)

8-allyl-amino-boron-dipyrromethene (Formula 2) was synthesized according to Reaction 2 as follows.

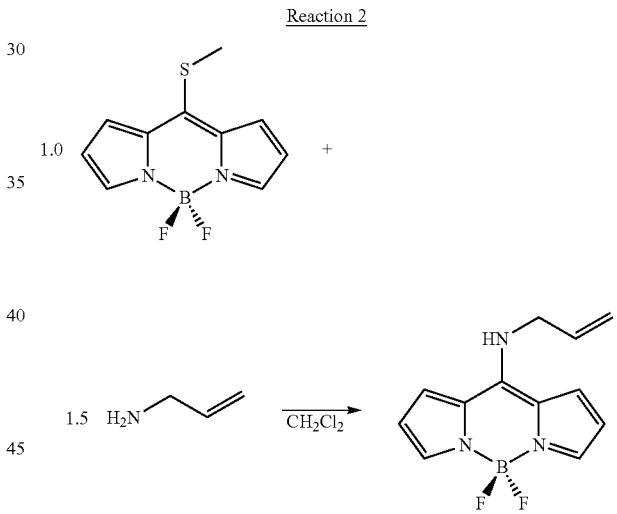

Reaction 2

1.0 equivalent (10 mg, 0.0408 mmol) of thiomethyl boron dipyrromethene was placed in a 50 mL flask and dissolved with 2 mL of dichloromethane. Subsequently, 1.5 equivalents of allylamine (2.32 mg, 0.0612 mmol) were added. The reaction mixture was stirred using a magnetic stirrer over a hot plate stirrer at 25° C. The reaction was completed in 60 minutes with a 90% yield. It materialized as fluorescent yellow crystals. CCD (30% AcOEt/Hexanes) $R_f$=0.19 cm; UV-Vis: $\lambda_{abs}$=400 $\lambda_{flu}$=456 (methanol), p.d. 131.0-132.0° C.; IR (KBr, cm$^{-1}$): 728, 928, 943, 1037, 1055, 1090, 1145, 1227, 1337, 1389, 1558, 1592, 2341, 2359, 2854, 2924, 2958, 3390; $^1$H NMR (200 MHz, CDCl3) δ: 4.36 (2H, m, J=5.6), 5.47 (2H, dd, J=16.8, 10.8 Hz), 6.05 (1H, m, J=6.8 Hz), 6.47 (3H), 7.05 (2H, s), 7.63 (2H, s). $^{13}$C NMR (50 MHz, CD$_3$CN), δ: 49.85, 113.97, 115.20, 116.88, 118.31, 122.90, 124.88, 126.31, 132.30, 132.59, 135.30, 150.20.

EXAMPLE 3

Synthesis of 8-methyl-amino-boron-dipyrromethene (Formula 3)

8-methyl-amino-boron-dipyrromethene (Formula 3) was synthesized according to Reaction 3 as follows.

Reaction 3

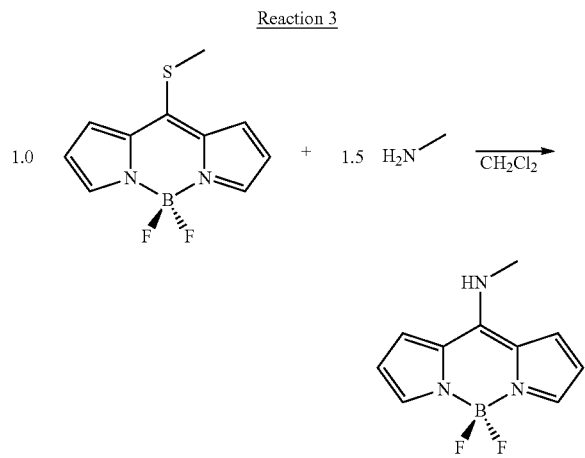

1.0 equivalents (80 mg, 0.3361 mmol) of thiomethyl boron dipyrromethene were placed in a 50 mL flask and dissolved with 2 mL of dichloromethane. Subsequently, 1.5 equivalents of methylamine (15.6 mg, 0.5042 mmol) were added. The reaction mixture was stirred using a magnetic stirrer over a hot plate stirrer at 25° C. The reaction was complete in 50 minutes with a 90% yield. It materialized as yellow crystals. CCD (30% AcOEt/Hexanes) $R_f$=0.09 cm; UV-Vis: $\lambda_{abs}$=394 $\lambda_{flu}$=438 (methanol) p.d. 199.0-201.0° C.; IR (KBr, cm$^{-1}$): 636, 728, 754, 888, 941, 975, 1043, 1083, 1167, 1231, 1277, 1389, 1455, 1563, 1603, 3365; $^1$H NMR (200 MHz, CDCl$_3$) δ: 3.36 (3H, d, J=5.8 Hz), 6.36 (1H, s), 6.56 (1H, s), 6.86 (2H, s), 7.2 (1H, s), 7.5 (1H, s), 7.74 (1H, s); $^{13}$C NMR (75.5 MHz, CD$_3$CN), δ: 32.81, 112.54, 113.81, 114.82, 121.94, 123.34, 124.6, 130.0, 137.37, 148.83.

EXAMPLE 4

Synthesis of 8-amino-boron-dipyrromethene (Formula 4)

8-amino-boron-dipyrromethene (Formula 4) was synthesized according to Reaction 4 as follows:

Reaction 4

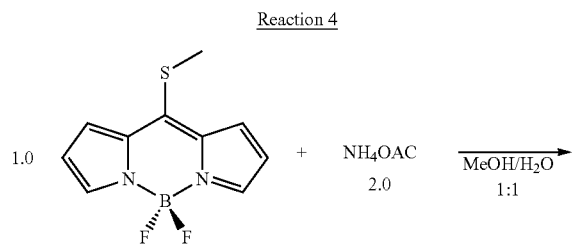

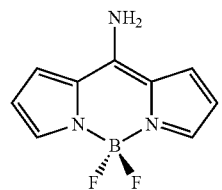

1.0 equivalent (80 mg, 0.3361 mmol) of thiomethyl boron dipyrromethene was placed in a 50 mL flask and dissolved with 1 mL of water and 1 mL of methanol. Subsequently, 2.0 of ammonium acetate (38 mg 0.5042 mmol) as an amine were added. The reaction mixture was stirred using a magnetic stirrer over a hot plate stirrer at 60° C. The reaction was complete in 120 minutes with a 91% yield. It materialized as yellow crystals. CCD (30% AcOEt/Hexanes) $R_f$=0.07 cm; UV-Vis: $\lambda_{abs}$=398 $\lambda_{flu}$=444 (methanol) p.d. 160.0-162.0° C.; IR (KBr, cm$^{-1}$): 521, 579, 726, 757, 944, 1023, 1041, 1076, 1148, 1277, 1306, 1401, 1457, 1567, 1659, 3113, 3273, 3369, 3459; $^1$H NMR (200 MHz, CDCl$_3$) δ: 6.19 (2H, s), 6.49 (2H, s), 7.10 (2H, s), 7.65 (2H, s); $^{13}$C NMR (75.5 MHz, CD$_3$CN), δ: 115.49, 119.84, 125.29, 135.0, 150.86.

EXAMPLE 5

Synthesis of methyl ester of 8-L-leucine dipyrromethene (Formula 6)

Methyl ester of 8-L-leucine dipyrromethene (Formula 6) was synthesized according to Reaction 5 as follows:

Reaction 5

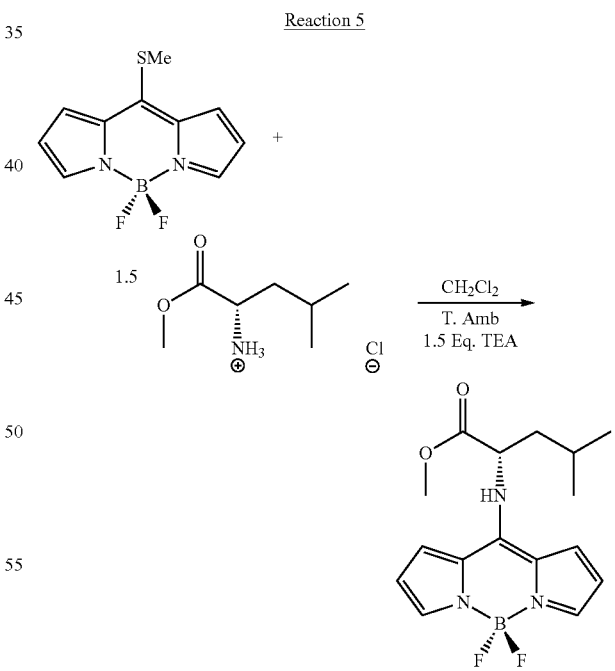

Into a new vial with a magnetic stirrer were added thiomethyl boron dipyrromethene (100.00 mg, 0.42 mmol, 1.0 eq.) and L-leucine methyl ester hydrochloride (114.49 mg, 0.63 mmol, 1.50 eq). Next, 3 mL of dichloromethane (CH$_2$Cl$_2$) were added. The system was stirred until complete dissolution was achieved. Finally triethylamine (TEA) (63.78 mg, 0.63 mmol, 1.50 eq.) was added. The reaction was vigorously and constantly stirred, and the vial was closed with a lid to avoid solvent evaporation. The reaction was complete after 135 min reaction time with a 94% yield. It materialized as an amber colored oil. CCD (30% AcOEt/Hexanes) Rf=0.75. $^1$H NMR (200 MHz, CDCl$_3$) δ 7.63 (2H, s), δ 7.08 (2H, s), δ 6.97 (1H, d), δ 6.47 (2H, s), δ 4.8 (1H, c), δ 3.8 (3H, s), δ 1.94 (2H, t), δ 1.74 (1H, q), δ 1.2 (2H, s), δ 1.04 (3H, d), δ 0.94 (3H, d). $^{13}$C NMR (75.5 MHz, CDCl$_3$) δ 171.75, δ 147.649, δ 115.01, δ 57.39, δ 53.41, δ 41.39, δ30.46, δ29.82, δ 25.27, δ22.63, δ 22.2.

EXAMPLE 6

Synthesis of ethylic ester from 8-β-alanine dipyrromethene (Formula 7)

Ethylic ester from 8-β-alanine dipyrromethene (Formula 7) was synthesized according to Reaction 6 as follows:

Reaction 6

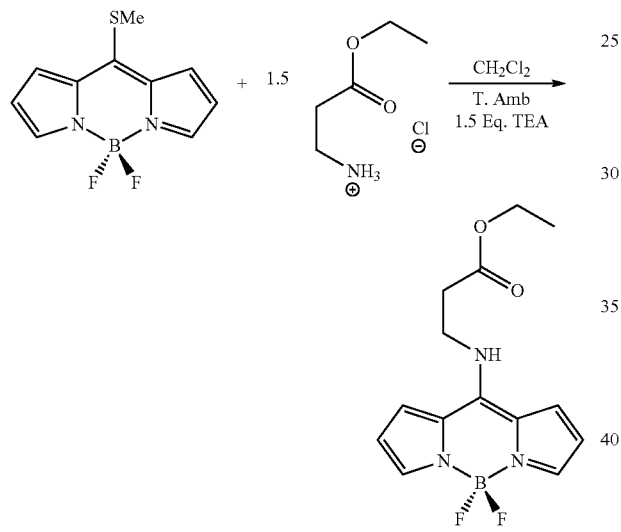

Into a new vial with a magnetic stirrer were added thiomethyl boron dipyrromethene (100.00 mg, 0.42 mmol, 1.0 eq.) and β-alanine hydrochloride methyl ester (96.81 mg, 0.63 mmol, 1.50 eq). Next, 3 mL of dichloromethane (CH$_2$Cl$_2$) were added. The system was stirred until complete dissolution was achieved. Finally, triethylamine (TEA) (63.78 mg, 0.63 mmol, 1.50 eq.) was added. The reaction was vigorously and constantly stirred, and the vial was closed with a lid to avoid solvent evaporation. The reaction was complete in 15 minutes with a 71% yield. It materialized as light yellow solids. CCD (30% AcOEt/Hexanes) Rf=0.39. $^1$H NMR (200 MHz, CDCl$_3$) δ 7.61 (3H, s), δ 7.03 (2H, s), δ 6.45 (2H, s), δ 4.25 (2H, c), δ 3.95 (2H, c), δ 2.8 (2H, t), δ 1.3 (3H, t). $^{13}$C NMR (75.5 MHz, CDCl$_3$/CD$_6$CO), δ 170.98, δ 148.4, δ 61.17, δ 42.38, δ32.37, δ 13.94.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:
1. An 8-amino boron dipyrromethene having formula 1, 2, 3, 4, 6, or 7:

Formula 1

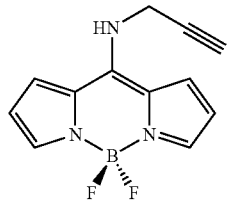

Formula 2

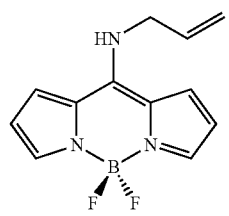

Formula 3

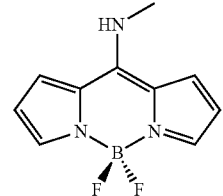

Formula 4

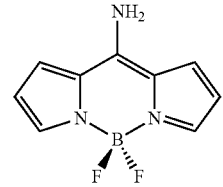

Formula 6

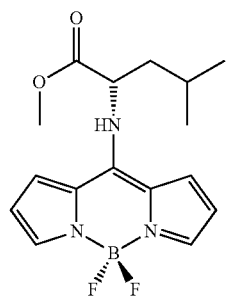

Formula 7

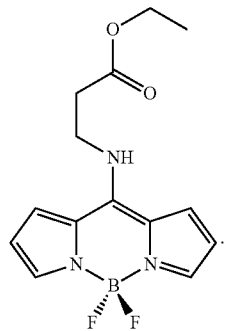

2. The 8-amino boron dipyrromethene according to claim 1, wherein the 8-amino boron dipyrromethene exhibits a high laser efficiency with emission in the blue region of the electromagnetic radiation spectrum.

3. The 8-amino boron dipyrromethene according to claim 2, wherein the 8-amino boron dipyrromethene has Formula 1 and has a quantum efficiency close to unity.

4. The 8-amino boron dipyrromethene according to claim 1, wherein the 8-amino boron dipyrromethene is obtained by substitution of the thiomethyl group in an 8-thiomethyl boron dipyrromethene precursor with an amine or ammonium source.

5. The 8-amino boron dipyrromethene according to claim 4, wherein the amine or ammonium source is selected from the group consisting of propargylamine, allylamine, methylamine and ammonium acetate.

6. The 8-amino boron dipyrromethene according to claim 4, wherein the amine or ammonium source is an amine ester.

7. A method of preparing an 8-amino boron dipyrromethene, comprising reacting 8-thiomethyl boron dipyrromethene with an amine or ammonium source to effect substitution of the thiomethyl group with the amine or ammonium source.

8. The method according to claim 7, wherein the reaction proceeds in about 1 hour with a yield of greater than about 90%.

9. The method according to claim 7, wherein the amine or ammonium source is selected from the group consisting of propargylamine, allylamine, methylamine and ammonium acetate.

10. The method according to claim 7, wherein the amine or ammonium source is an amine ester.

11. The method according to claim 7, wherein the 8-amino boron dipyrromethene has formula 1, 2, 3, 4, 6, or 7:

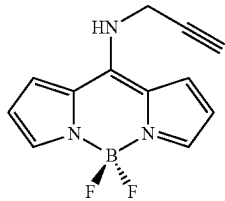

Formula 1

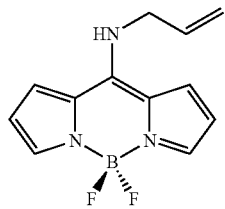

Formula 2

-continued

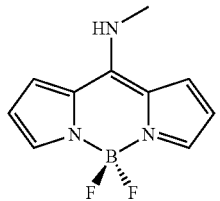

Formula 3

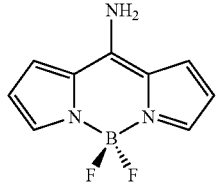

Formula 4

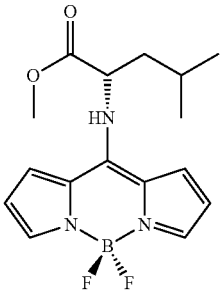

Formula 6

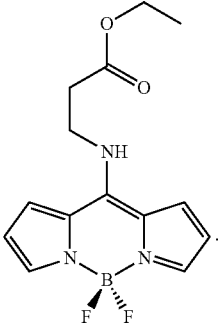

Formula 7

* * * * *